United States Patent
Molenda (10) Patent No.: US 11,783,929 B2
(45) Date of Patent: Oct. 10, 2023

(54) GRAPHICAL GENERATION AND RETRIEVAL OF MEDICAL RECORDS

(71) Applicant: Matthew A. Molenda, Monclova, OH (US)

(72) Inventor: Matthew A. Molenda, Monclova, OH (US)

(*) Notice: Subject to any disclaimer, the term of this patent is extended or adjusted under 35 U.S.C. 154(b) by 184 days.

(21) Appl. No.: 17/364,145

(22) Filed: Jun. 30, 2021

(65) Prior Publication Data

US 2021/0326808 A1    Oct. 21, 2021

Related U.S. Application Data

(63) Continuation of application No. 14/537,460, filed on Nov. 10, 2014, now abandoned.

(60) Provisional application No. 62/068,016, filed on Oct. 24, 2014, provisional application No. 61/906,192, filed on Nov. 19, 2013, provisional application No. 61/901,735, filed on Nov. 8, 2013.

(51) Int. Cl.
  *G16H 15/00*    (2018.01)
  *G16H 10/60*    (2018.01)
  *G06Q 10/10*    (2023.01)

(52) U.S. Cl.
  CPC .......... *G16H 15/00* (2018.01); *G06Q 10/10* (2013.01); *G16H 10/60* (2018.01)

(58) Field of Classification Search
  CPC ........ G16H 15/00; G16H 10/60; G16H 50/50; G06Q 10/10
  See application file for complete search history.

(56) References Cited

U.S. PATENT DOCUMENTS

| | | | | |
|---|---|---|---|---|
| 7,680,678 B2* | 3/2010 | Funahashi | ............... | G16H 30/20 705/2 |
| 8,112,289 B2* | 2/2012 | Yang | ..................... | G06Q 10/10 705/2 |
| 8,311,848 B2* | 11/2012 | Subash | .................. | G06Q 10/10 705/2 |
| 9,078,621 B2* | 7/2015 | Garner | ................... | G06T 7/0012 |
| 2012/0069968 A1* | 3/2012 | Core | .................... | A61N 5/1049 378/206 |

* cited by examiner

*Primary Examiner* — Robert A Sorey
*Assistant Examiner* — Kristine K Rapillo
(74) *Attorney, Agent, or Firm* — Daniel M. Cohn; Howard M. Cohn (57) ABSTRACT

Systems and method are provided for generating a record of a medical procedure. A system includes a processor and a non-transitory computer readable medium. The medium includes a graphical user interface configured to display a graphic representing an anatomical region of a patient and accept a gesture from a user comprising a selected procedure and, diagnosis when appropriate, and a location on the displayed anatomical region. A knowledge base stores a plurality of templates, each comprising a set of fields. A record generation engine selects an associated one of the plurality of templates according to each of the selected procedure and, diagnosis when appropriate, and the location on the displayed anatomical region and populates the set of fields associated with the selected template. A database interface formats the populated template into a database record suitable for an electronic health records database associated with the system.

17 Claims, 6 Drawing Sheets

GRAPHICAL GENERATION AND RETRIEVAL OF MEDICAL RECORDS

RELATED APPLICATIONS

This application is a continuation of U.S. patent application Ser. No. 14/537,460, filed Nov. 10, 2014, which claims priority from each of U.S. Provisional Patent Application Ser. No. 61/901,735, filed Nov. 8, 2013, U.S. Provisional Patent Application Ser. No. 61/906,192, filed Nov. 19, 2013, and U.S. Provisional Patent Application Ser. No. 62/068, 016, filed Oct. 24, 2014. Each of these applications is hereby incorporated by reference in their entireties for all purposes.

TECHNICAL FIELD

This invention relates to medical systems, and more particularly, to graphical generation of medical records.

BACKGROUND OF THE INVENTION

An electronic health record (EHR), or electronic medical record (EMR), is a systematic collection of electronic health information about an individual patient or population. It is a record in digital format that is theoretically capable of being shared across different health care settings. In some cases, this sharing can occur by way of network-connected, enterprise-wide information systems and other information networks or exchanges. EHRs may include a range of data, including demographics, medical history, medication and allergies, immunization status, laboratory test results, radiology images, vital signs, and personal statistics like age and weight.

SUMMARY OF THE INVENTION

In accordance with an aspect of the present invention, a system is provided for generating a record of a medical procedure. The system includes a processor and a non-transitory computer readable medium. The medium includes a graphical user interface configured to display a graphic representing an anatomical region of a patient and accept a gesture from a user comprising a selected procedure and a location on the displayed anatomical region. A knowledge base stores a plurality of templates, each comprising a set of fields. A record generation engine selects an associated one of the plurality of templates according to each of the selected procedure and the location on the displayed anatomical region and populates the set of fields associated with the selected template. A database interface formats the populated template into a database record suitable for an electronic health records database associated with the system.

In accordance with another aspect of the present invention, a method is provided for recording a medical procedure. A user is allowed to make a gesture on a specific location on a displayed graphic representing an anatomical region of a patient. The gesture representing a selected procedure performed at that location. One of a plurality of available templates is selected according to each of the selected procedure and the specific location. At least one of the set of fields associated with the selected template is populated with text describing the selected procedure and the specific location. The populated template is formatted into a database record suitable for an electronic health records database.

In accordance with an aspect of the present invention, a system is provided for generating a record of a medical procedure. The system includes a processor, a camera, and a non-transitory computer readable medium. The medium includes a graphical user interface configured to display a graphic representing an anatomical region of a patient and accept a gesture from a user comprising a selected procedure and a location on the displayed anatomical region. A knowledge base stores a plurality of templates, each comprising a set of fields. A record generation engine selects an associated one of the plurality of templates according to each of the selected procedure and the location on the displayed anatomical region and populates the set of fields associated with the selected template. A database interface formats the populated template into a database record suitable for an electronic health records database associated with the system.

A first subset of at least one of the set of fields is populated with text escribing the selected procedure and the location on the displayed anatomical region and a second subset of at least one of the set of fields is populated with a first photograph of the anatomical region of the patient taken by the camera prior to the selected procedure and additional photographs of the anatomical region of the patient taken by the camera during and after the selected procedure. A database interface is configured to format the populated template into a database record suitable for an electronic health records database associated with the system.

DETAILED DESCRIPTION

The Anatomy Mapper is a software application configured to provide an interactive graphical display of the human surface anatomy to enhance accurate medical labeling and record keeping. Anatomy Mapper provides a number of tools for medical professionals to more easily and accurately chart anatomical features and issues related to a patient. For example, Anatomy Mapper is configured to annotate predefined mapped images and/or imported images or photos (e.g., of patients), save annotated images with associated modifiable text, and export into Electronic Health Records (EHRs) by communicating with EHR systems or, alternatively, save annotated images and text into a stand-alone device running the EHR or Anatomy Mapper. The system allows mapped images to generate lists of treatment locations, biopsy sites, procedure/surgery sites, imaging and photograph sites, patient exam findings, or other relevant information and document a patient encounter using anatomic locations/annotations as the note's foundation, for example, by automatically generating a procedure note by clicking on a specific anatomical area. Users can be allowed to add or customize features/modules as needed.

Errors or lack or precision in medical records can results from a lack of knowledge of correct terminology by person filling out labels, a lack of effort (e.g., it is easier to write/type "face" than "Left Paramedian Lower Forehead"), lack of understanding of consequences of ambiguous labeling (e.g., surgery at an incorrect location or delay in surgery). The Anatomy Mapper provides precision in labeling anatomical areas by utilizing graphical representations that automatically provide associated annotations in text. The system also provides documentation of procedures performed via selecting a labeled anatomical area, and complimenting photographs or other media taken of anatomical areas, with the ability to import and annotate images collected of the patient. For example, if a dermatologist performs cryosurgery on twenty lesions, they may be more likely to be reimbursed for their work if they can document locations for all twenty lesions. With pending changes in healthcare, it may eventually no longer be enough to say "cryosurgical destruction to twenty lesions" and expect appropriate reimbursement. In addition to static images, Anatomy Mapper can include annotated, rotatable, and scalable 3D and vector models, as well as a variety of medical mapping tools for specialized practice.

In general, the application may display icons or cartoon figures of a variety of anatomical drawings. The icons may include rough outlines of anatomical features such as a face, or may display more detailed anatomy such as the helix, anti-helix, lobule and other structures of an ear. In one implementation, these standardized images can be overlaid on top of patient photos. For example, the eyebrows, pupils, nostrils, chin, and ears of the standardized image can be matched to the corresponding features in the photo to provide a mapped overlay. A user may select a category of anatomical features based on an icon or a tab presented in the graphical interface. A user may select a rough outline icon so he or she may be presented with a more detailed icon. The user may select a portion of an icon and have a display window display text related to the selected portion. The text displayed in the window may include a standardized descriptor of the selected anatomical portion. The standardized descriptor may be in accordance with local, national, and/or international formats. The text in the window may be saved to a patient specific health care record in a health care database. The data transferred by the application may be provided to the health care database in a structured data format. The data format may conform to local, national, and/or international standards. The patient specific record may include patient specific information including patient name, ID number, address, date of birth, physician names, previous procedures, and the like.

Additionally, the user may be presented with a defined list of procedures associated with the selected anatomical portion. The user may choose one or more of such procedures to save in a patient record. The user may also add free text, voice, video, imaging, and other forms of media to annotate the patient record regarding the selected procedures. The user may also enter alternative procedures not among those presented to the user. The user may also provide annotations to the icons in the form of text and/or symbols to indicate approximate location of anatomical features associated with the patient.

The user may upload one or more graphical images into the application. Such graphical images may include photographs of a portion of a patient related to one or more medical procedures. An example of a graphical image may be a photograph of a patient's skin lesion. The graphical images may be stored as part of a patient record in a health care database. Graphical images may include photographs, computer renderings, or representation of such images (e.g., through vector rendering). The graphical images may be two-dimensional or three dimensional. The graphical images may include a series of images indicating patient features over a period of time. The graphical images may include, as an example, a series of photographs of a patient's mole over time to determine if the mole has transformed into a malignancy. Computerized pattern recognition algorithms may be applied to the images to assist the user in detecting changes over time. The graphical images may include images of a patient's skin lesion before and after surgery. The graphical images may include still images or video images. The images may be presented to the user as part of the application. The user may employ touch screen display, mouse controls or other input means to annotate the graphical images. Such annotations may include graphical symbols and/or text. Vocal recordings supplied by the user may also be linked as annotations to the graphical images.

The graphical images, such as photographed records of the patient, may be linked to the related icons presented to the user to get a map overlay on the patient image. Annotations to the application icons may be transferred to equivalent locations on the images of the patient's anatomy. The patient images may be registered with the icons by means of image transformation utilities associated with the application. Alternatively, the user may indicate which patient image features correspond to equivalent features on the icons, thereby registering the image with the icon in a manual fashion.

The application may also be linked to a printer. The application may cause the printer to print out a document or a label. The label may include identifying information (such as a barcode or QR code) that may indicate a patient identification, as well as an indication of a portion of a patient's anatomy. The label may be applied to the patient at an anatomical location consistent with the information on the label. A photograph may be taken of the patient's anatomical location including at least a portion of the patient and the label. The photograph may be uploaded into the application which may automatically read the label information and use that to properly store the photograph with the patient's medical records.

The application may also use the information related to patient procedures and provide codes related to patient billing for the procedures. The billing code may be stored with the patient medical records in a health care database. The application may also use the information related to a patient procedure anatomic site to provide unified diagnostic code also related to anatomic site. The unified diagnostic code may be stored with the patient medical records in a health care database. A graphical image, such as a photograph, may be taken of a supply (pharmaceutical, device, or material) container used for a patient procedure. The photograph may include labeling and identification information related to the supply used in the procedure include the name of the supply, a lot number, an expiration date, and other identifying information related to the supply used.

The graphical images of all types entered into the application may have a variety of annotations associated with them. The annotations may be stored as separate text entries or in a structured format into a patient record in a health care database. The annotations may be saved graphically as additional graphical layers to the graphical images.

The application may also store patient intake data. The intake data may be entered into the application by a health care professional as part of an in-office patient visit or may be linked to an EHR or other data repository to import the intake data. The information may be entered by the patient into a device such as an iPad or computer at the physician's office that may be associated with the application. The patient entry may be by text (such as by keyboard), touch, voice, or other input methods. The patient may enter the data into a remote device, such as through the patient's personal desktop or laptop computer. The patient's computer may also include the application. Alternatively, the patient's computer may access a secured website and enter the data into the application running on the server providing the website. In one implementation, the system can be configured to accept a signature or other authorization from the patient granting consent for treatment. For example, this verification can be done from fingerprint, retinal scan, facial recognition, electronic biosignatures, or other, similar means.

The application may be part of a suite of applications, each application tailored to a particular medical specialty. Each application may have its own defined lexicon of anatomy and procedure terms for entry into a health care database. Each medical specialty related application may have its own set of icons related to anatomical portions of a patient's body. Examples of such specialties may include dermatology and internal medicine. The applications may include human specific application. The applications may also include veterinary applications. The applications may include dental applications.

The suite of applications may be purchased for use by a physician, physician practice, a hospital or other medical establishment. Derivative applications may also be purchased by consumers, educational institutions, and technology companies such as EHR vendors. The applications may be purchased separately in a modular fashion or bundled together. The applications may be specific to a type of device (such as a computer or an iPad) and/or a specific device operating system. The applications may be paid for on a subscription basis. The applications may reside on a central server under the control of a provider, and may be accessed by paying a per-transaction fee, a per-seat fee, or on a time-base fee structure.

Figure 1:
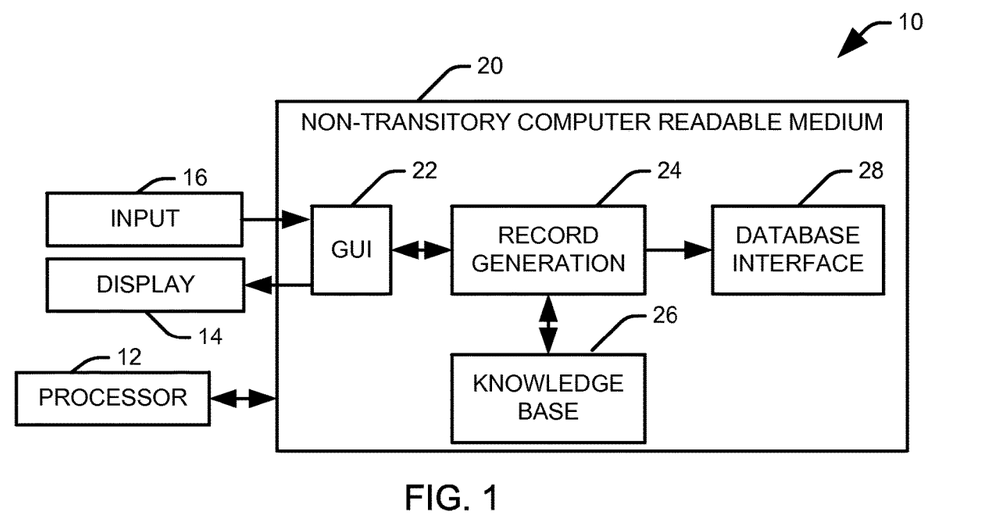
FIG. 1 illustrates a system in accordance with an aspect of the present invention.

FIG. 1 illustrates a system 10 in accordance with an aspect of the present invention. The system 10 includes a processor 12, a display 14, an input device 16, and a non-transitory computer readable medium 20 storing machine executable instructions. The instructions stored on the medium 20 include a graphical user interface (GUI) 22 configured to display a graphic representing an anatomical region of a patient and accept a gesture from a user comprising a selected procedure and a location on the displayed anatomical region. It will be appreciated that the graphical user interface 22 can include a number of input tools designed to assist the user. In one example, procedures can be selectable from a dropdown or similar menu, with submenus associated with each procedure allowing the user to select parameters such as agent or material types, dosages, and repetitions of a given step. It will be appreciated that the various submenus can be specific to a particular procedure, such that a first procedure will have different associated submenus than a second procedure.

A knowledge base 24 stores a plurality of templates, each comprising a set of fields, with a first template of the plurality of templates having a different set of fields than a second template of the plurality of templates. A record generation engine 26 is configured to select an associated one of the plurality of templates according to each of the selected procedure and the location on the displayed anatomical region and populate the set of fields associated with the selected template, at least one of the set of fields comprising text describing the selected procedure and the location on the displayed anatomical region. Accordingly, the information selected by the user via the graphical selection and the various toolbars and menus is recorded using the selected template, allowing a record of the procedure to be quickly and accurately generated. A database interface 28 is configured to format the populated template into a database record suitable for an electronic health records database associated with the system. It will be appreciated that one or more images associated with the record can also be stored in the database system. In one implementation, these images include both raw images and annotated images of the anatomical location associated with treatment.

Figure 2:
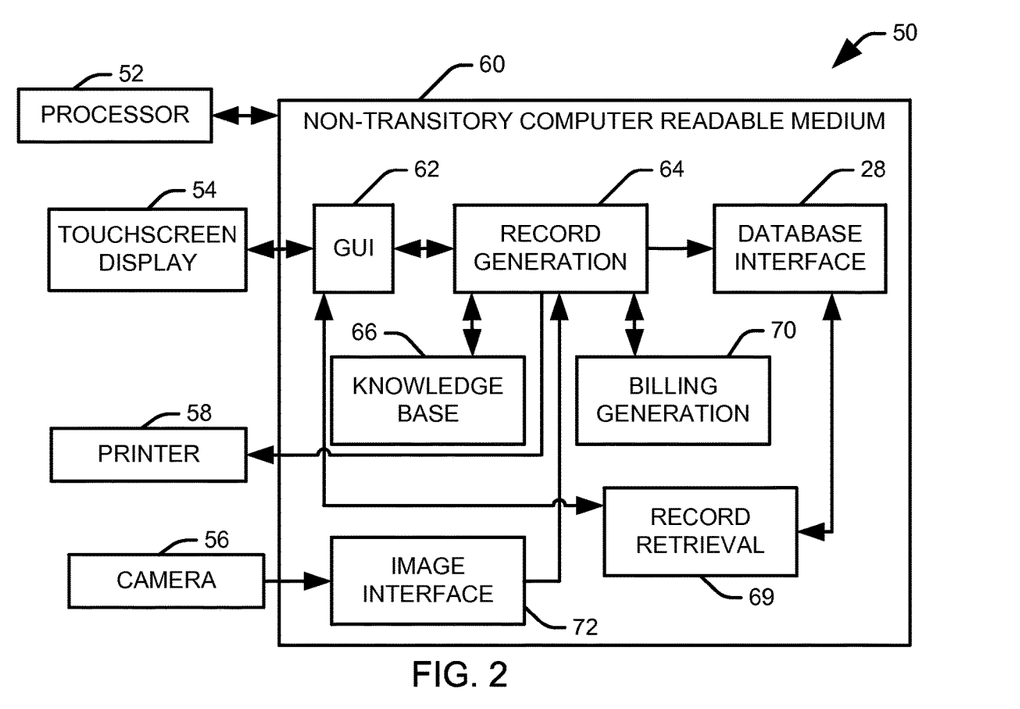
FIG. 2 illustrates a system in accordance with an aspect of the present invention.

FIG. 2 illustrates a system 50 in accordance with an aspect of the present invention. The system 50 includes a processor 52, a touchscreen display 54, a camera 56, a printer 58 and a non-transitory computer readable medium 60—storing machine executable instructions. The instructions stored on the medium 60 include a graphical user interface (GUI) 62 configured to display a graphic representing an anatomical region of a patient on the touchscreen display and accept a gesture from a user comprising a selected procedure and a location on the displayed anatomical region. It will be appreciated that the graphical user interface 62 can include a number of input tools designed to assist the user. In one example, procedures can be selectable from a dropdown or similar menu, with submenus associated with each procedure allowing the user to select parameters such as agent or material types, dosages, and repetitions of a given step. For example, where the selected procedure is a botulinum toxin injection, the menu could allow the user to select a number of units and a multiplier indicating an automatically converted number of units injected at a given site.

A knowledge base 64 stores a plurality of templates, each comprising a set of fields associated with a given procedure and location. A record generation engine 66 is configured to select an associated one of the plurality of templates according to each of the selected procedure and the location on the displayed anatomical region and populate the set of fields associated with the selected template. A database interface 68 formats the populated template into a database record suitable for an electronic health records database associated with the system. Since each database record is associated with an anatomical location, it will be appreciated that the records, and any information linked to those records, can be retrieved via the location. Accordingly, the GUI 62 can be configured to allow a user to retrieve a timeline of clinical activity, for example, via a record retrieval engine 69, for a selected location on the displayed graphic or a particular diagnosis (generating multiple timelines if the diagnosis occurred in multiple anatomic locations; for example, basal cell carcinoma), for example, via a dropdown menu. The timeline can give a data and brief description for each procedure, encounter, image or diagnoses associated with the selected location in the order they occurred as well as links to or thumbnail images (that can be expanded) of supplementary material associated with the diagnosis or procedure. For example, these supplementary materials can include physician reports, images of the treatment site at various times, pathology reports, digital slides, images of supply containers used in the procedure, and other relevant medical documents.

To this end, the record generation engine 66 being configured to fill at least one of the set of fields with a first multimedia item associated with the anatomical region of the patient acquired prior to the selected procedure and additional multimedia items of the anatomical region of the patient taken during and after the selected procedure. It will be appreciated that, the multimedia items can include standalone images, selected frames from videos, videos, digital Slides, documents (operative reports, pathology reports, phone call messages, videos, diagnoses, billing codes, nurse visits, other encounters, consent forms, patient verification of consent to treat the diagnosis at the anatomic site, etc.), and other forms of media stored within the database. This is particularly useful in a Mohs surgical procedure and similar procedures in which the treatment is provided in stages. For these procedures, the set of fields can store at least a first photograph of the anatomical region of the patient taken prior to the surgical procedure, a second photograph of the anatomical region of the patient taken during the surgical procedure, and a third photograph of the anatomical region of the patient taken after the surgical procedure. In one implementation, the record generation engine 66 generates digital labels and drawings overlaid over a portion of each of the photographs listing at least the anatomical region, a name of the patient, and a medical record number. Further, since each record is tied to a specific location, when a list of locations is altered by a user, for example, by adding a location, removing a location, or rearranging existing the locations, data associated with each location is automatically transferred with the location.

The printer 58 is responsive to the record generation engine 66 and configured to print a label including at least the anatomical region, a name of the patient, a date of birth of the patient, a differential diagnosis, a chronological specimen number, letter, or code, and a medical record number. This label can be applied to paper records for the client to efficiently record the details of the procedure and automatically link the documentation to the appropriate anatomic location. In one implementation, the label can include a bar code, QR code, or similar coding conveying either information about the patient procedure or diagnosis, for example, as a billing or diagnosis code, or a link to such information.

A billing generation engine 70 is configured to aggregate a plurality of selected procedures and locations from the graphical user interface to represent a patient interaction and assign a billing value to each of the selected procedures according to the selected procedure. From these assigned billing values, a bill is generated for the patient interaction. For example, the set of fields associated with the selected template comprises a total number of units of a substance associated with the procedure and a cost per unit for the substance. The billing generation engine 70 calculates a total price for the substance. Another example is when a procedure utilizes a different code based on how many times the procedure is performed. The billing generation engine 70 can calculate the correct code(s) to utilize.

Finally, an image interface 72 is configured to process a received image from the camera 56 and provide it to the record generation engine 66. For example, the image interface 72 can filter, compress, and otherwise condition the image for use in the database system. In one implementation, the image interface 72 can include appropriate image recognition software extracting at least one of the set of fields associated with the selected template from a received image of a supply label or a patient identification label associated with the selected procedure.

Figure 3:
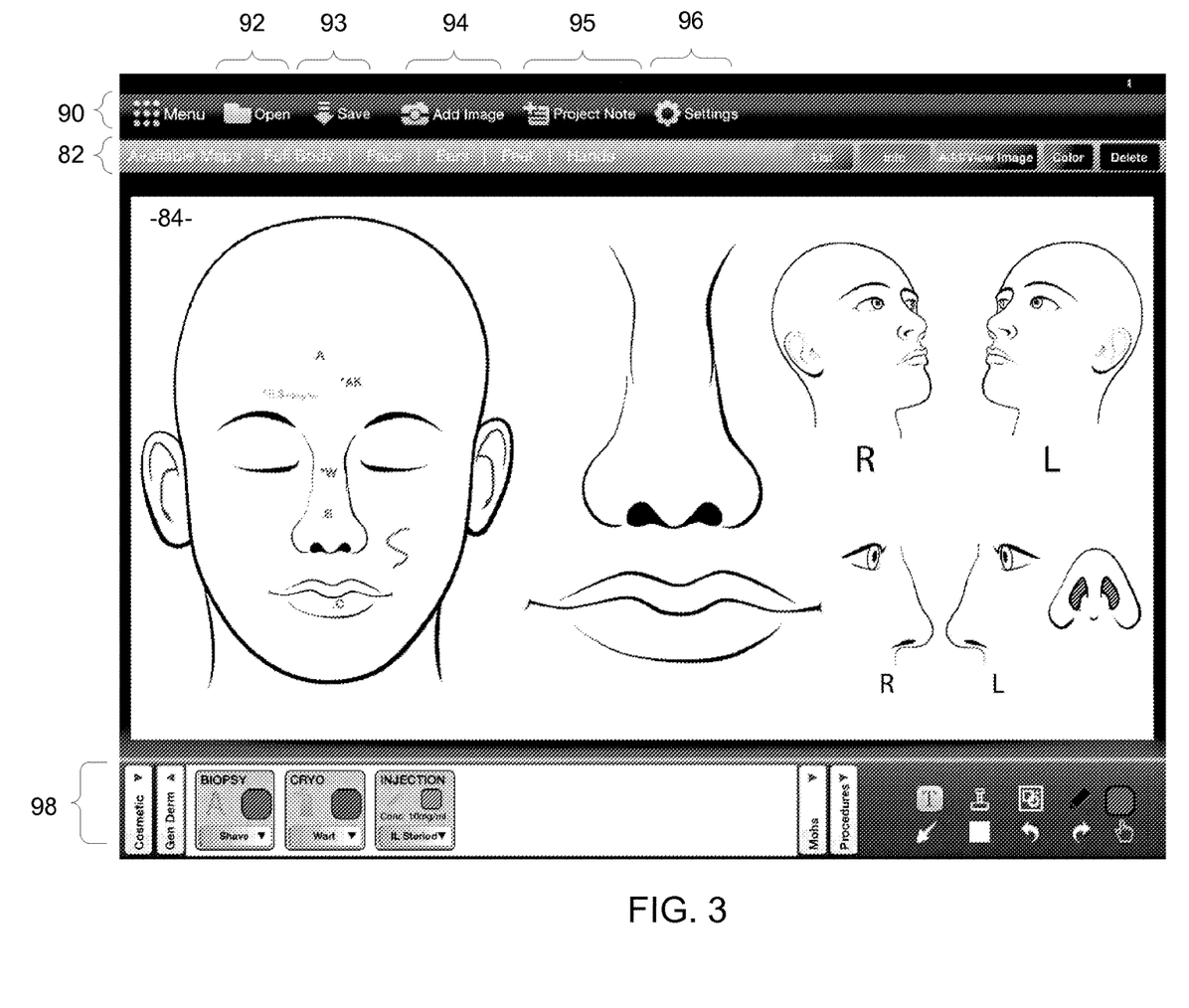
FIG. 3 is a screenshot of one example of an implementation of the present invention.

FIG. 3 is a screenshot of one example of an implementation of the present invention. The screenshot illustrates a tab bar 82 configured to allow the user to select a general anatomical location and a graphic window 84 configured to show graphics associated with the selected location. A first toolbar 90 allows the user to interact with the images.

For example, one function of the system is opening an image to draw on, represented by the open folder 92. This could either be an image taken on a tablet device such as the iPad, a previously annotated image or record, or an image imported from another source such as the hard drive or external camera. Annotated images can be saved, via a save function 93, to a hard drive or a Photo roll, exported to XML or other structured or unstructured data formats, or exported to PDF. These can be represented as options that scroll out to right or the user can set a default option saved in a cookie. An add image function 94 can be used to capture an image at a camera and import it into the graphic area for annotation. Maps may be overlaid over captured images to define anatomic sites on captured images, utilizing landmarks within the image by computerized or manual alignment. A project note function 95 can be used to add annotations to a given procedure or set of related procedures. A settings function 96 allows the user to change configuration options for the system, including altering the appearance and functions of the toolbars 90 and 98.

A second toolbar 98 provides tools are used to label sections of anatomy. This section uses anatomic terms when available with the image. Custom colored alphabetical and symbol labels are generated for different procedures, such as shave biopsies, punch biopsies, shave removals, electrodesiccation and curettage, skin tag removal and removal of seborrheic keratoses. In one implementation, this is implemented as a procedure labeler, generating drop-down boxes for each site indicated within the text.

Figure 4:
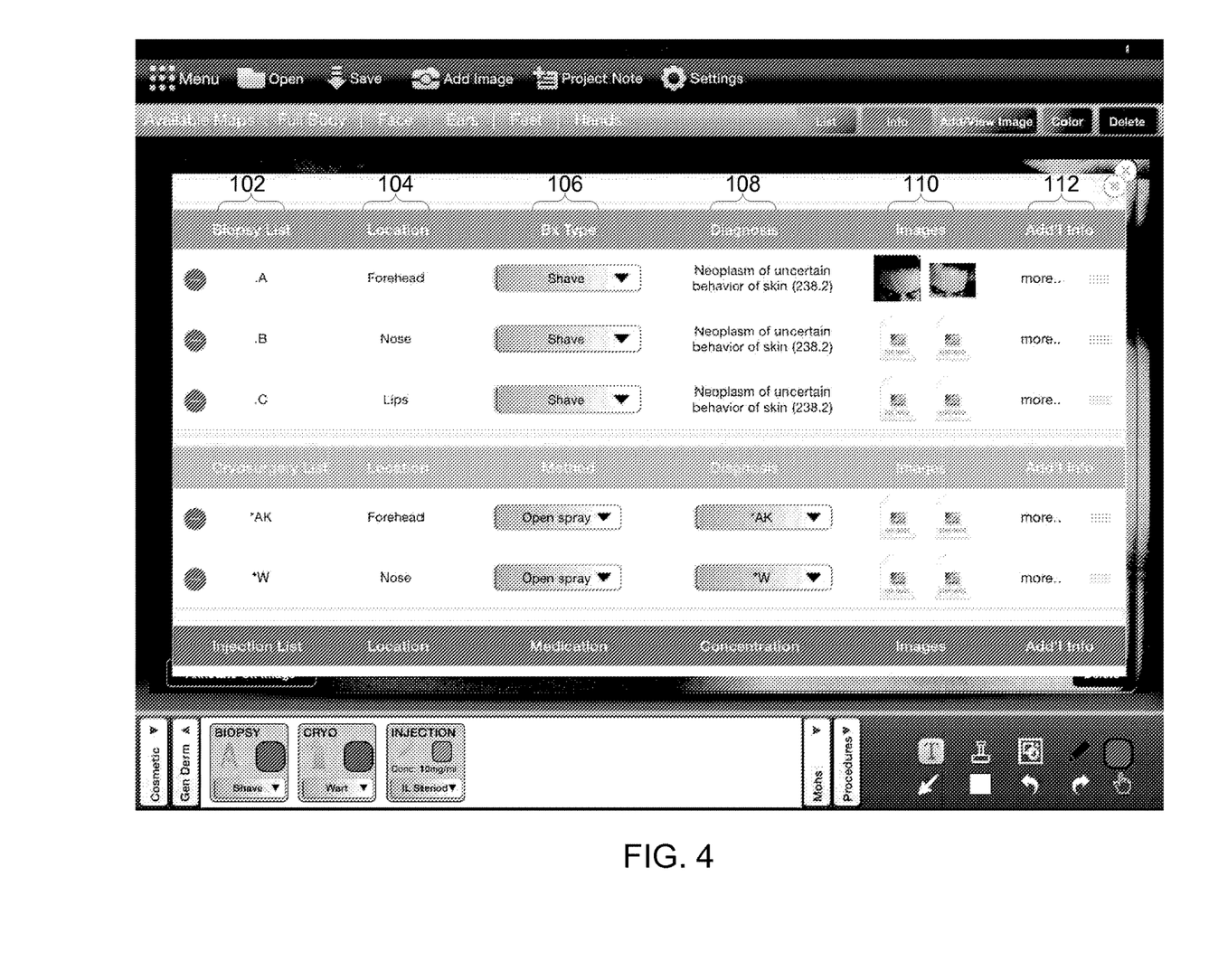
FIG. 4 is a screenshot of a procedure labeler function.

FIG. 4 is a screenshot of a procedure labeler function. The function includes a label column 102 indicating labeled sites within the graphic. Site labels can have various labeling options, such that users can make a list with capital letters, lowercase letters, numbers, and/or Roman numerals. These labels will automatically reorder when an existing site is deleted or added. A location column 104 gives a general location of the site in text, and a Bx column 106 allows the user to enter a procedure or plan for that site, for example, via a drop-down menu filtered by general procedure or plan type and location. A diagnosis column 108 allows a user to select or enter an appropriate diagnosis for the site, and an images column 110 allows the user to supplement the entry with photographs or videos of the site. An additional information column 112 allows the user to enter any additional text that might be useful for the record.

In one implementation, the application of filler can be represented by a custom-colored symbol, such as a colored line with an arrow and an abbreviation for the filler substance for a linear injection or a circle for a deep injection. Various products, with associated abbreviations, can include Restylane (ˆRESL), Perlane (ˆPERL), Juvederm Ultra (ˆJUVx), Juvederm Ultra Plus (ˆJUVx+), Radiesse (ˆRAD), Belotero (ˆBEL), Prevelle Silk (ˆPSi), Sculptra (ˆSCU), Artefiiii (ˆART), Autologous Fat (ˆFat), Silicone (ˆSi), Zyplast (ˆZyp), Zyderm (ˆZyd), Cosmoderm (ˆCod), Cosmoplast (ˆCop), and Other (ˆOther). The anatomical location can be represented from an initial tap in generating the line. Other options that can be selected for these procedures can include a number of syringes used of each product, an amount in each syringe of each product, a lot number, and an expiration date for each syringe. In one implementation, one or more of these parameters can be determined from a photo taken of a label for the product, although it will be appreciated that they can be entered manually. Some fillers can have additional details provided via the menus, like a concentration for Sculptra or a date of harvest for fat.

In the procedure labeling, cryosurgery is represented by a custom-colored asterisk with alphanumeric and symbolic abbreviations. Actinic keratoses can be represented as a simple *AK, warts can be represented as "*w", and other conditions can have other annotations. Injections of neurotoxins will be annotated with a custom colored "sharp" carat, with ^D representing Dysport, ^B representing Botox, and so forth. It will be appreciated that the user can enter a custom product name for injections, for example, limited to eight characters. A text giving the concentration text can be provided next to the product, for example, in a smaller subscript. The toxin can be entered with a number of parameters, such as a lot number, expiration, a number of vials, a total number of units used, a cost per unit, and a dilution. It will be appreciated that some of these parameters can be determined automatically from the lot number, such as from an appropriate product database.

In one implementation, when a user taps and releases a toxin injection, the tap value is placed along with the smaller subscript abbreviation of the toxin used. However, when a user taps and does not release, the values are displayed, and the user drags his or her finger to the value they want to select, then they release. The value they selected is placed at the initial tap site along with the smaller subscript abbreviation of the toxin used. The toxin menu can also include a multiplier option. When the user taps and releases the multiplier button, the value (× multiplier) is placed on the image/map along with the smaller subscript abbreviation of the toxin used. This item is the active item till the user clicks or taps elsewhere, so it can be moved or deleted easily. In another implementation, a value wheel is used, with the user can setting the initial value of the wheel, and each subsequent value is an integer multiple of the initial value. Finally, a quick select implementation allows the user to tap the multiplier and drag to the value to be selected. The quick selected value (x multiplier) is placed on the map along with the smaller subscript abbreviation of the toxin used. Again, the selected item is the active item till the user clicks elsewhere, so it can be moved or deleted easily. It will be appreciated that each toxin can have an associated default or initial value for its concentration, amount of toxin, and multiplier.

There will also be tools to allow the user to add more freeform annotations to the diagram. These tools can include a drawing tool, represented by pencil icon that functions as a solid line drawing tool with selectable line width and color. A straight-line tool can be provided as part of this tool. A scalpel illustration function can be provided for drawing quick flap designs in a distinctive way with dotted lines. In one implementation, the tools that cross anatomic sites, such as the scalpel tool, can be used to generate text for a medical record. For example, a procedure note might say "an incision was made from the Right Lateral Canthus up to the Right Superior Temple near the Hairline, and then the incision traveled down along the Right Pre-Auricular Cheek to the Right Angle of the Jaw." The user can select the color of the lines and the pattern or style of the line. The scalpel illustration can use a default width with variable line styles.

A shape tool allows the user to draw ellipses, rectangles, triangles, stars, hearts and similar shapes, include both solid shapes and outlines. The width, style, and color of the outline, as well as a fill color, can be selected by a user. These options can be changed in a shape menu. The most recently placed shape can be movable, scalable, and rotatable without using the select tool if the user taps and holds within that shape area. A new shape can be placed if the user is working outside of the shape area. When a shape is selected, the user has the option to delete or resize or rotate it. A free text tool allows the user to enter text with customizable font size and color. In one implementation, the default color is bright green. The text can be designed to be deleted quickly, for example, via a delete icon at a corner of the text. An arrow tool generates an arrow with a back of the arrow at mouse-click (or finger press) to a point of the arrow at mouse or finger release. As user is dragging, an arrow extends in the precise direction of drag in real time. A stamp tool allows the user to place predefined stamps on the image. As soon as the user places the stamp, the stamp is active and if the user clicks in the area, the user can move, pinch-zoom resize, and rotate the stamp. An icon can be provided to quickly delete the stamp. One of the pop-up context menu items might also include a "Crop" tool to crop a stamp.

Certain items may have optional properties that can be associated with them, such as medication strength, manufacturer, lot number, expiration, dilution, and number of units in each injection. When the user clicks on an item that is already there, a delete icon and an icon that opens a menu for adjustment of the item properties is provided. When a user clicks the icon to display item properties, they can enter the lot number, expiration, manufacturer, dilution, number of units in this injection, or any other applicable properties. Some applicable properties may be added with a photograph or extracted data from a photograph. There will also be a check box that is checked by default that applies some or all of the selected properties to all instances of the item.

Figure 5:
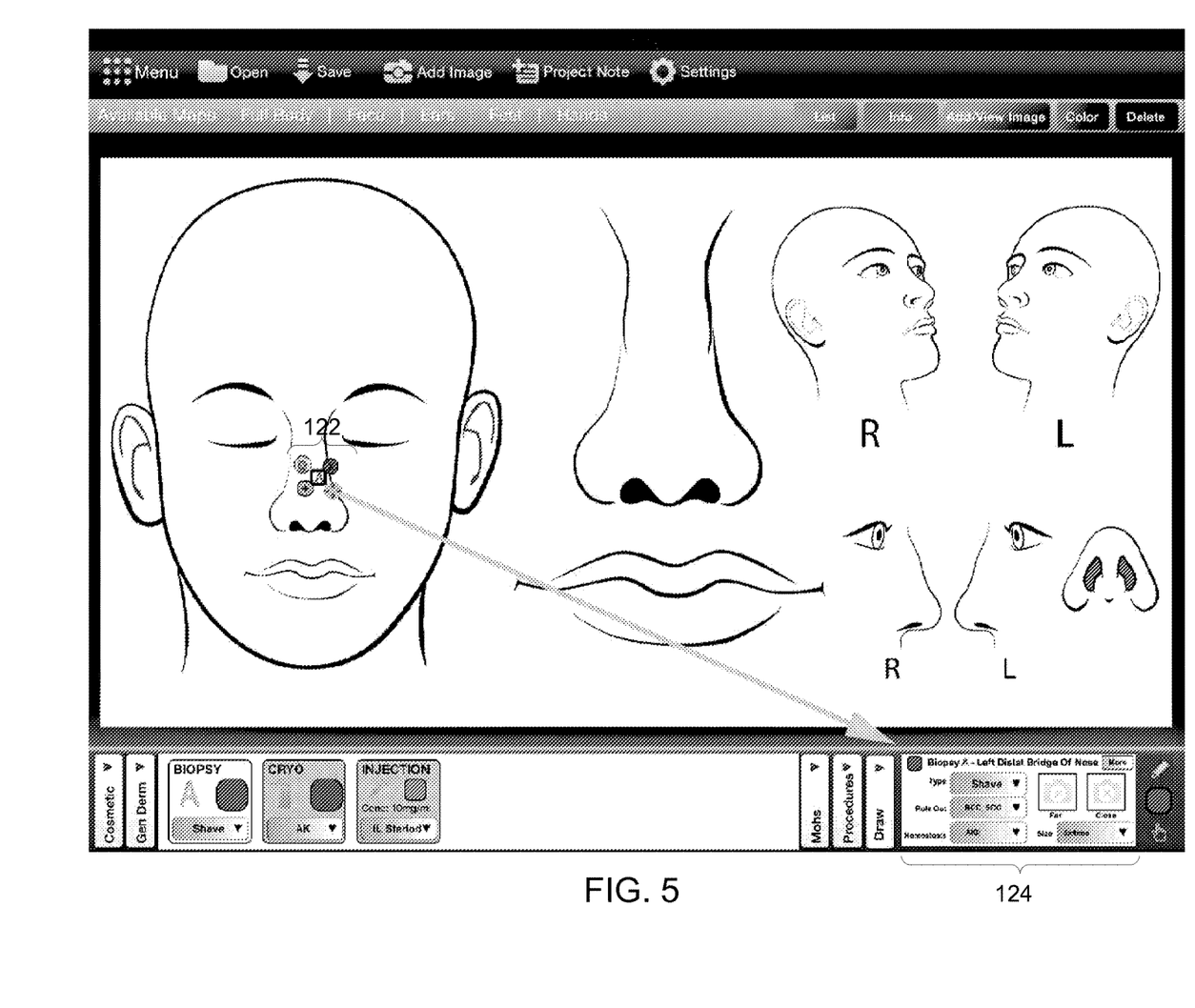
FIG. 5 is a screenshot showing a quick menu associated with an anatomical site marker.

The tools for modifying the image and other menus can be accessed directly by tapping a given site. FIG. 5 is a screenshot showing a quick menu 122 associated with an anatomical site marker, "A". In the illustrated example, a context menu 124 has been selected and is displayed at the bottom of the screen. Via the quick menu 122, the user can quickly cycle through multiple menus, facilitating access to the various tools provided in the system.

Figure 6:
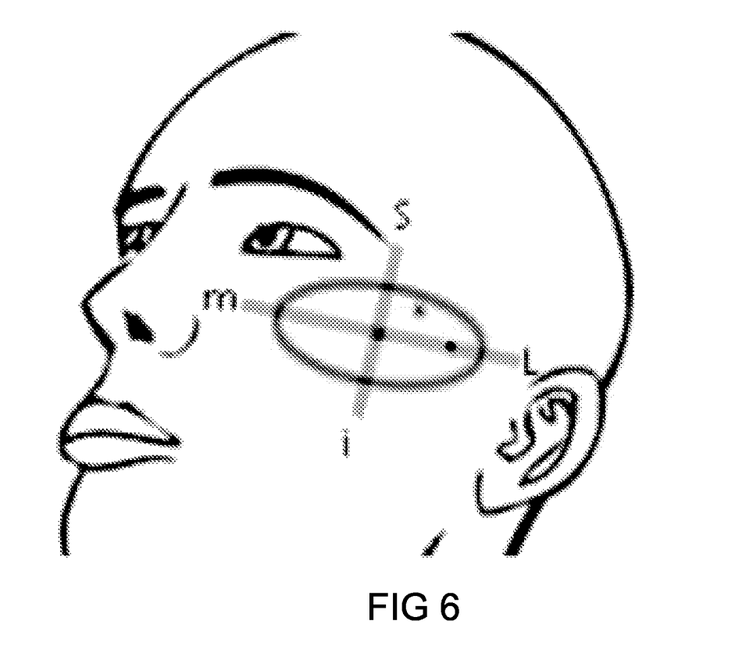
FIG. 6 is a screenshot showing a function for precisely locating an anatomical site.

In one implementation, relatively large regions can be used to define anatomic locations, with automated assistance provided to determine a more specific location. For a simple example, if an oval region is defined as a "left malar cheek", subcoordinates of the region can be defined according to proximity and direction away from center region. For example, a selected position can be triangulated it on two or three axes, for example, the superior and inferior (S/I) axis, the medial/median and lateral (M/L) axis, and the anterior and posterior (A/P) axis. In an example provided as FIG. 6, we could get a reading for a first location, indicated as a dot on "left lateral malar cheek" and a second location, indicated as an "X" as the "left mid superior malar cheek." The terms used to describe the location (e.g., mid, lateral, superior, etc.) can have a percentage associated with them indicating how far away from the center they fall. So, each annotation acts as its own frame of reference, with a center as well as two or more axes defined. The percentage deviation from the center of each unit will show us how close the annotation is to the border and how close it is to a neighboring anatomic subunit. While this is more complicated than defining regions in a concrete fashion, such concrete definitions raise concern about accuracy and interpretation of "borders" between imperfectly bordered surface anatomy sites.

Figure 7:
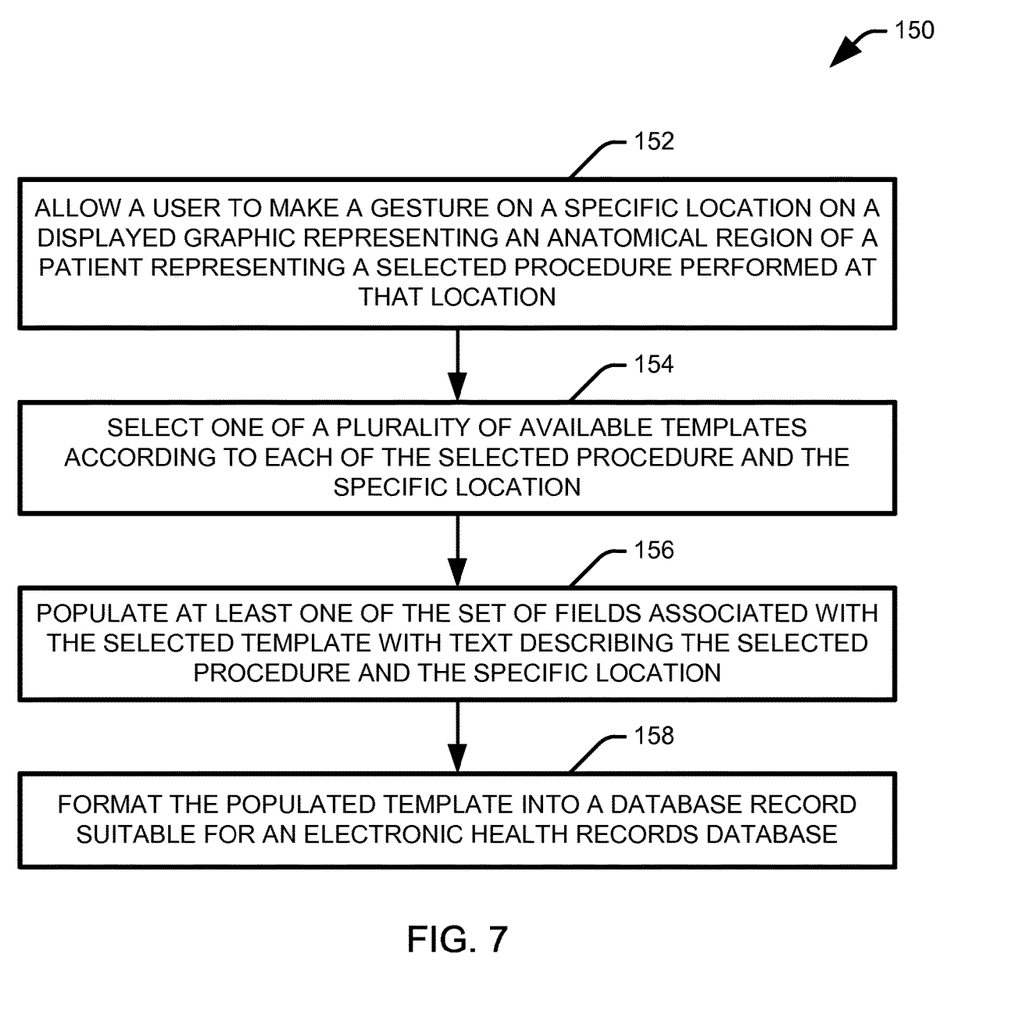
FIG. 7 illustrates a method for recording a medical procedure in accordance with an aspect of the present invention.

FIG. 7 illustrates a method 150 for recording a medical procedure in accordance with an aspect of the present invention. At 152, a user is allowed to make a gesture on a specific location on a displayed graphic representing an anatomical region of a patient. For example, the user can make selections at an associated graphical user interface such that the gesture represents a selected procedure performed at that location. At 154, one of a plurality of available templates from an associated knowledge base is selected according to each of the selected procedure and the specific location.

At 156, at least one of the set of fields associated with the selected template is populated with text describing the selected procedure and the specific location. In one implementation, additional fields can be filled with images taken of the patient and/or supplies associated with the procedure. For example, a first field can include a first photograph of the anatomical region of the patient taken prior to the selected procedure with one or more other fields including additional photographs of the anatomical region of the patient taken during and after the selected procedure. A digital label can be overlaid over a portion of each of the first and second photographs listing at least the anatomical region, a name of the patient, and a medical record number. Alternatively, the system can process a received image of a product label associated with the selected procedure and extract text for at least one of the set of fields associated with the selected template from the received image. At 158, the populated template is formatted into a database record suitable for an electronic health records database.

Figure 8:
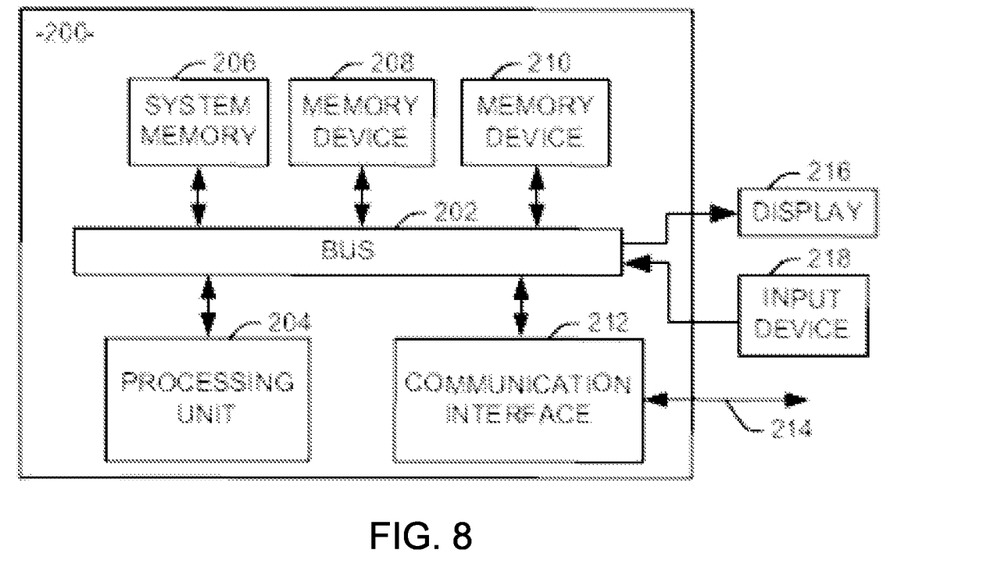
FIG. 8 is a schematic block diagram illustrating an exemplary system of hardware components capable of implementing examples of the systems and methods disclosed herein, such as the anatomy mapper system described previously.

FIG. 8 is a schematic block diagram illustrating an exemplary system 200 of hardware components capable of implementing examples of the systems and methods disclosed herein, such as the anatomy mapper system described previously. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard, touch screen, and/or a mouse). The system bus 202 can be in communication with the processing unit 204 and the system memory 206. The additional memory devices 208 and 210, such as a hard disk drive, server, stand-alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port. Wireless connections, such as Near Field Communication, Bluetooth, Wifi, are also possible to supporting devices such as label printers and the EHR database. In one implementation, the wireless connection can be used with a device such as a cellphone, watch, or other device wearable by the patient to provide a verified digital signature. Further, such a connection could be used to transfer relevant photos from a patient's personal electronic device directly into their record and associate it with an anatomic site.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of an anatomy mapper system in accordance with the present invention. Computer executable logic for implementing the composite applications testing system resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the scope of the appended claims.

The invention claimed is:

1. A system for generating an improved patient specific record for at least one specific anatomic location using proximity and direction away from a center point, the system comprising:
   a processor for the calculation of proximity and overlap zones defined by a coordinate system comprising a center point on the anatomical location, multiple axes, and a percentage deviation from the center point wherein an output of said processor identifies a specific coordinate defined anatomic location representative of a patient;
   a graphical user interface configured to receive a gesture wherein the gesture identifies specific patient information;
   a display wherein a user can view and select at least one specific coordinate defined anatomic location representative of the patient;
   a record generation engine being configured to fill a set of fields with the specific patient information; and
   a non-transitory computer readable medium, storing machine executable instructions executable by the processor, the machine executable instructions configured to:

display a graphical user interface with a graphic representing the anatomical region of the patient;

identify at least one specific coordinate based on the defined anatomic location on the displayed graphic representative of a location on the patient where at least one patient specific event occurs;

generate at least one frame of reference for each patient specific input using proximity and direction away from the specific coordinate on at least two custom axes;

receive a patient specific input from the user wherein the patent specific input is a gesture wherein the gesture identifies specific patient information representative of a procedure, diagnosis, treatment, observation or documentation identified or created by the user;

retrieve from a knowledge base storing a plurality of templates, each comprising a set of fields, with a first template of the plurality of templates having a different set of fields than a second template of the plurality of templates wherein said templates each identify an input of a unique event or location attribute;

select an associated one of the plurality of templates according to each of the selected event and the location on the displayed representative anatomical region;

populate the set of fields associated with the selected template, at least one of the set of fields comprising text describing the selected event and the location on the displayed representative anatomical region;

fill at least one of the set of fields with a first multimedia item associated with the anatomical region of the patient taken prior to the selected procedure and additional multimedia items associated with the anatomical region of the patient taken during and after the selected procedure wherein the multimedia items have maps overlaid with defined terminology;

link the selected templates wherein said inputs become a combined record;

generate a digital label for the combined record listing at least the anatomical region, a name of the patient, and a medical record number;

format the combined record into a database record suitable for an electronic health records database associated with the system; and display a complete patient history of the anatomical region wherein said specific coordinate defined anatomic locations within the anatomic region are defined according to proximity and direction away from a center point allowing for each patient specific input from the user to act as its own frame of reference to neighboring and underlying anatomic regions, based on user identified or created events.

2. The system of claim 1, the machine executable instructions further comprising a billing generation engine configured to aggregate a plurality of selected procedures and anatomical locations from the graphical user interface to represent a patient interaction, assign a billing value to each of a plurality of sets of at least one of the selected procedures according to the selected procedures and the associated anatomical locations, and generate a bill for the patient interaction.

3. The system of claim 2, wherein the set of fields associated with the selected template comprises a total number of units of a cosmetic or pharmaceutical substance associated with the procedure and a cost per unit for the cosmetic or pharmaceutical substance, the billing generation engine being further configured to calculate a total price for the cosmetic or pharmaceutical substance from the total units and the cost per unit.

4. The system of claim 3, the record generation engine being configured to fill at least one of the set of fields with a first multimedia item associated with the anatomical region of the patient taken prior to the selected procedure and additional multimedia items associated with the anatomical region of the patient taken during and after the selected procedure wherein the multimedia items have maps overlaid with defined terminology wherein the multimedia items are linked to the anatomical region and automatically translate with any alteration made by user in the patient record to the anatomical region.

5. The system of claim 4, further comprising a touchscreen display configured to allow the user to interact with the graphical user interface.

6. The system of claim 5, wherein the selected procedure comprises an administration of a specified number of units of a cosmetic or pharmaceutical substance to the anatomy of the patient.

7. The system of claim 6, wherein the selected procedure is a Mohs surgical procedure, the set of fields comprising at least a first photograph of the anatomical region of the patient taken prior to the Mohs surgical procedure, a second photograph of the anatomical region of the patient taken during the Mohs surgical procedure, and a third photograph of the anatomical region of the patient taken after the Mohs surgical procedure whereby being linked to the same anatomical region automatically links the photographs.

8. The system of claim 7, further comprising a printer responsive to the record generation engine and configured to print a label including one or more of the anatomical regions, a name of the patient, a date of birth of the patient, a differential diagnosis, a chronological specimen number, letter, or code; and a medical record number.

9. The system of claim 8, wherein the graphical user interface is further configured to display a menu based on the selected procedure, the user selecting at least one parameter for the set of fields associated with the selected template from the menu.

10. The system of claim 9, wherein the graphical user interface is further configured to display a first menu when a first procedure is selected and a second menu when a second procedure is selected, the first and second menus having different associated options based on the anatomic location, diagnosis, and proposed treatment.

11. The system of claim 10, further comprising an image interface configured to process a received image of a supply label or patient identification label associated with the selected procedure and to extract at least one of the set of fields associated with the selected template from the received image.

12. The system of claim 11, wherein the graphical user interface is configured to allow the user to select an anatomic region to receive a timeline of records associated at the anatomic region, incorporate multimedia items taken before, during and after a procedure, and diagnoses associated with the anatomic region.

13. A method for recording a performed medical procedure at a specific anatomic location comprising:

displaying a graphical user interface with a graphic representing the anatomical region of a patient;

identifying at least one specific coordinate based on the defined anatomic location on the displayed graphic representative of a location on the patient where at least one patient specific event occurs;
generating at least one frame of reference for each patient specific input using proximity and direction away from the specific coordinate on at least two custom axes;
inputting a patient specific data comprising of at least a selected procedure performed on the patient at said specific defined anatomic location;
retrieving from a knowledge base storing a plurality of templates, each comprising a set of fields, with a first template of the plurality of templates having a different set of fields than a second template of the plurality of templates wherein said templates each identify a unique event or location attribute;
selecting an associated one of the plurality of templates according to each of the selected event and the location on the displayed representative anatomical region;
populating the set of fields associated with the selected template, at least one of the set of fields comprising text describing the selected event and the location on the displayed representative anatomical region;
filling at least one of the set of fields with a first multimedia item associated with the anatomical region of the patient taken prior to the selected procedure and additional multimedia items associated with the anatomical region of the patient taken during and after the selected procedure wherein the multimedia items have maps overlaid with defined terminology;
linking the selected templates wherein said inputs become a combined record;
generating a digital label for the combined record listing at least the anatomical region, a name of the patient, and a medical record number;
formatting the combined record into a database record suitable for an electronic health records database associated with the system; and
filling at least one of the set of fields with a first multimedia item associated with the anatomical region of the patient taken prior to the selected procedure and additional multimedia items associated with the anatomical region of the patient taken during and after the selected procedure wherein the multimedia items have maps overlaid with defined terminology;
formatting the combined record into a database record suitable for an electronic health records database;
generating a complete patient history of the anatomical region wherein said specific coordinate defined anatomic locations within the anatomic region are defined according to proximity and direction away from a center point in multiple custom axes allowing for each patient specific input from the user to act as its own frame of reference to neighboring and underlying anatomic regions, based on user identified or created events; and
storing the complete patient history associated with the defined anatomical location.

14. The method of claim 13, further comprising:
processing a received image of a product label associated with the selected procedure; and
extracting at least one of the set of fields associated with the selected template from the received image.

15. A computer-implemented system for generating a patient specific record based on inputs by users of at least one performed medical procedure at a specific anatomic location comprising:
a processor wherein the processor is configured to identify a specific coordinate defined anatomic location representative of the patient defined by a coordinate system comprising a center point on the anatomical location, multiple axes, and a percentage deviation from a center point, wherein calculation of proximity and overlap zones in relation to neighboring and underlying defined anatomic locations can occur;
a graphical user interface configured to receive a gesture wherein the gesture identifies specific patient information;
a display wherein the user can view and select at least one specific coordinate defined anatomic location representative of the patient;
a camera;
a record generation engine being configured to fill a set of fields with the specific patient information; and
a non-transitory computer readable medium, storing machine executable instructions executable by the processor, the machine executable instructions for executing a method comprising:
displaying a graphical user interface with a graphic representing the anatomical region of the patient;
identifying at least one specific coordinate based on the defined anatomic location on the displayed graphic representative of a location on the patient where at least one patient specific event occurs;
generating at least one frame of reference for each patient specific input using proximity and direction away from the specific coordinate on at least two custom axes;
receiving a patient specific input from the user wherein the patent specific input is a gesture wherein the gesture identifies specific patient information representative of a procedure, diagnosis, treatment, observation or documentation identified or created by the user;
retrieving from a knowledge base storing a plurality of templates, each comprising a set of fields, with a first template of the plurality of templates having a different set of fields than a second template of the plurality of templates wherein said templates each identify an input of a unique event or location attribute;
selecting an associated one of the plurality of templates according to each of the selected event and the location on the displayed representative anatomical region;
populating the set of fields associated with the selected template, at least one of the set of fields comprising text describing the selected event and the location on the displayed representative anatomical region;
filling at least one of the set of fields with a first multimedia item associated with the anatomical region of the patient taken prior to the selected procedure and additional multimedia items associated with the anatomical region of the patient taken during and after the selected procedure wherein the multimedia items have maps overlaid with defined terminology;
linking the selected templates wherein said inputs become a combined record;
generating a digital label for the combined record listing at least the anatomical region, a name of the patient, and a medical record number;
formatting the combined record into a database record suitable for an electronic health records database associated with the system; and generating a complete patient history of the anatomical region wherein said specific coordinate defined anatomic locations within the anatomic region are defined according to proximity and direction away from a center point allowing for each patient specific input from the user to act as its own frame of reference to neighboring and underlying anatomic regions, based on user identified or created event; and storing the complete patient history associated with the defined anatomical location.

16. The system of claim 15, the machine executable instructions further comprising a billing generation engine configured to aggregate a plurality of selected procedures, diagnoses and anatomic locations from the graphical user interface to represent a patient interaction, assign a billing value to each of the selected procedures according to the selected procedures, diagnoses and the associated locations, and generate a bill for the patient interaction.

17. The system of claim 16, the anatomical location defined by a coordinate system comprising a center point on the anatomical location, multiple axes, and a percentage deviation from a center point, wherein calculation of proximity and overlap zones in relation to neighboring and underlying defined anatomic locations can occur.

* * * * *